United States Patent [19]
Avitall

[11] Patent Number: 5,242,441
[45] Date of Patent: Sep. 7, 1993

[54] DEFLECTABLE CATHETER WITH ROTATABLE TIP ELECTRODE

[76] Inventor: Boaz Avitall, 4868 N. Ardmore Ave., Milwaukee, Wis. 53217

[21] Appl. No.: 840,026

[22] Filed: Feb. 24, 1992

[51] Int. Cl.$^5$ .................. A61B 17/36; A61B 5/04; A61N 1/00
[52] U.S. Cl. ..................... 606/41; 128/642; 607/122
[58] Field of Search .............. 128/419 P, 642, 784, 128/786; 606/41

[56] References Cited

U.S. PATENT DOCUMENTS

| | | |
|---|---|---|
| 4,369,248 | 9/1985 | Narula . |
| 4,564,024 | 1/1986 | Wohler, Jr. ............. 128/419 S |
| 4,660,571 | 4/1987 | Hess et al. . |
| 4,671,649 | 2/1987 | Walinsky et al. . |
| 4,682,596 | 7/1987 | Bales et al. . |
| 4,785,815 | 11/1988 | Cohen . |
| 4,920,980 | 5/1990 | Jackowski ............ 128/642 |
| 4,960,134 | 10/1990 | Webster, Jr. . |

FOREIGN PATENT DOCUMENTS

0249631 9/1987 Fed. Rep. of Germany ........ 606/49

Primary Examiner—Lee S. Cohen
Assistant Examiner—Marianne Parker
Attorney, Agent, or Firm—Haugen and Nikolai

[57] ABSTRACT

A cardiac arrhythmia ablation catheter that has a highly flexible tubular distal segment particularly adapted for navigating and exploring a ventridular cardiac chamber forming a lumen through its length which connects to a distal electrode-carrying tip which is provided with an independently rotatable tip electrode mounted at the distal end tip of the distal tip section and adapted to engage and roll over the internal surface of a ventricular heart chamber of interest without rotation of the catheter itself. A wire deflection control system is provided to deflect the distal tip system of the distal catheter section in a controlled manner and a hand-operated control is provided to control the rotation of the rotatable tip electrode.

21 Claims, 2 Drawing Sheets

DEFLECTABLE CATHETER WITH ROTATABLE TIP ELECTRODE

BACKGROUND OF THE INVENTION

I. Cross-Reference to Related Application

Reference is made to applications Ser. Nos. 07/835,553, entitled BIPLANAR DEFLECTABLE CATHETER FOR ARRHYTHMOGENTIC TISSUE ABLATION, filed Feb. 14, 1992, now abandoned; and Ser. No. 07/840,162, entitled DEFLECTABLE LOOP ELECTRODE ARRAY MAPPING AND ABLATION CATHETER FOR CARDIAC CHAMBERS, filed Feb. 24, 1992, now abandoned of inventorship. Both of these cross-referenced applications also are directed to improved catheters.

II. Field of the Invention

The present invention is directed generally to an improved catheter for use in the field of cardiac arrhythmia ablation. More particularly, the invention is directed to the use of a rotating tip deflectable catheter system with greatly increased catheter tip maneuverability in the lateral plane, i.e., perpendicular to the catheter shaft, and especially when operating in the ventricular chambers. This allows the operator to direct the tip of the catheter in multiple directions and maneuver the catheter as close as possible to the site of the arrhythmogenic tissue to accomplish effective mapping and ablation.

III. Discussion of the Related Art

Normal cardiac pacing, in a healthy heart, is controlled by a special structure known as the sinoatrial node (SA node). This is the natural pacemaker of the heart and is a specialized tissue located within the muscle walls of the right atrium. The SA node provides impulses which dominate the inherent or natural rhythmic contractions of the heart atria and the ventricles. This dominance or control involves the transmission of ionic impulses through cardiac conduction pathways in the atria and the ventricles which cause the heart to contract and relax in an orderly sequence at a rate dictated by the SA node. This sequence ensures that blood flow to the systemic circulation or the pulmonary system will be maximized with each ventricular contraction. The SA node has its own inherent rate which can be modified by signals from the nervous system. In response to excitement, physical activity, etc., the sympathetic and parasympathetic nervous systems react to modify the rate.

A depolarization impulse begins with the SA node and spreads as an electrical wave from its location in the right atrium across to the left atrium and down toward the transition zone between the atrium and the ventricles where another node, known as the atrioventricular (A-V) node or junction, is located. This impulse conducts through the A-V node in a slower fashion and continues to a common pathway known as the Bundle of His between the right and left ventricles, then into multiple paths called right and left bundle branches, each bundle branch supplying one ventricle. These bundle branches then divide into an extensive network of finer paths of conducting tissue which spread from the inner to the outer surfaces of the heart and which are referred to as the Purkinje fibers. These fibers feed the depolarization impulse into all portions of the ventricular myocardium.

As long as this system is intact, impulses are transmitted normally and cardiac rhythm is maintained. The natural impulse or current flow in the cardiac conduction system, however, may be interrupted or altered by congenital defect, disease or injury which can cause the formation of scar tissue. When a sufficiently severe injury or a congenital defect is present in the cardiac conductive pathways or in the ventricular myocardium, the electrical impulses are not transmitted normally and rhythmic disturbances known as cardiac arrhythmias can occur. With respect to such disturbances, the term bradycardia is used to describe an abnormal slowing of the cardiac contractions and the term tachycardia is used to describe abnormally rapid heart action. While either of these conditions can endanger the life of the patient, tachycardia is the more serious, particularly in patients having underlying heart disease.

Ventricular tachycardia and other ventricular arrhythmias have been treated with a number of drugs such as lidocaine, quinidine and procainamide. In cases of excessive sympathetic nervous activity or adrenal secretion, Beta blocking drugs have been used. In cases where drug therapy has been ineffective in preventing tachyarrhythmias, certain surgical procedures have been used to ablate the arrhythmogenic tissue either from the atrium or the ventricles. This procedure involves extensive surgery in which an incision through the pericardium and heart muscle is made locate the arrhythmogenic tissue, which is then frozen or surgically removed to be replaced by scar tissue.

Because open-heart surgery is a high risk procedure which requires a prolonged period of hospitalization and recuperation, a less traumatic solution is needed. In response, catheters of various types have been devised and used for diagnosing and treating a number of cardiac abnormalities to avoid the trauma of open-heart surgery. For example, as a method for resolving atherosclerotic plaque build up, stenotic lesions are now routinely opened by the use of balloon angioplasty. In this procedure, a balloon carrying catheter is navigated through the patient's vascular system to the location of the stenosis. The balloon is inflated by fluid injected through a lumen of the catheter to apply pressure to the walls of the clogged vessel, thereby opening it.

Catheter devices have also been used to locate and ablate cardiac conduction pathways. One such device is shown in U.S. Pat. No. 4 785 815, in which a catheter tube carries at its distal end at least one electrode for sensing membrane potentials within the heart, together with a heating device for ablating at least a portion of the pathway located by the sensing device. Another thermal ablation catheter for microtransection or macrotransection of conduction pathways within the heart, which uses a resistive heating element at its distal end for highly localized treatment, is illustrated and described in U.S. Pat. No. 4 869 248. These devices are generally effective once the ablating element is properly positioned at the localized area of interest. A catheter device of the class described has also been developed which employs a single handle operated tip deflection wire. Such a device is disclosed in U.S. Pat. No. 4 960 134.

Electrophysiological catheter ablation procedures often have been hampered by the inability of the operator to maneuver the catheter tip to the precise location of the arrhythmogenic tissue. This problem is most pronounced in the ventricular chambers because of the high degree of trabeculation which forms the inner linings of the chambers. The mapping and ablation catheter tip often becomes wedged within the folds of the trabeculae. In an attempt to move the catheter, the operator must resort to applying torque to the shaft of the catheter which often leads to an abrupt dislodgment of the tip from its position to an undesirable remote location. This problem leads to prolonged and, at times, agonizing repeated attempts to maneuver and place the catheter into the appropriate location.

This is primarily a result of the limited maneuverability of the catheter tube itself. The catheter tube must have sufficient strength and stiffness to be guided through the vascular system to the vicinity of the tissue of interest. This construction does not allow the degree of flexibility at the tip of the catheter needed to perform intricate multidirectional manipulations in the highly localized areas involved. Available catheters are characterized by an inadequate control of fine movements and have tips that can be deflected only in planes parallel to the main catheter tube. They lack the ability for controlled lateral movement in planes perpendicular to that of the main catheter tube within the atria or the ventricles and to navigate the extremely rugged surfaces of the ventricular chambers inner lining (endocardium).

Most present cardiac tissue ablation procedures involve the use of radio frequency (RF) electrical current transmitted to the tissue via a catheter which is positioned as closely as possible to the arrhythmogentic site within the atria or ventricles. Radio frequency electrical current heats the tissue surrounding the catheter, creating a discrete dense lesion. In order for the patient to be cured of the arrhythmia, the lesion must be created in the area from which the arrhythmia originates. Improvement in the maneuverability of such devices could optimize precise positioning of the catheter prior to ablation.

SUMMARY OF THE INVENTION

The present invention provides a new catheter design which endows the catheter tip with increased flexibility. The increased flexibility involves the incorporation of a rotating tip deflectable system which allows control of the lateral movements of the catheter tip.

The catheter system of the present invention includes an elongated flexible tubular catheter having a proximal end, a distal end and a central lumen extending therebetween. The outside diameter of the catheter is such that it can be routed through the vascular system of a patient and into the heart chamber of interest to be treated. The main tubular catheter is typically 7-8 French in size. The distal portion of the main tubular section of the catheter in the present invention includes a flexible distal tip section fabricated from a highly flexible reinforced polymer tubing material, preferably polyethylene, which is connected to the main catheter tube. A portion of the flexible tubing extends inside the distal end of the main tubing section of the catheter.

The flexible distal tip section includes a metallic tip electrode which is preferably of a metal such as stainless steel or platinum, and, in one successful embodiment, is 16 mm long and 4 mm in diameter. The tip system electrode includes a rotating tip electrode and is connected to the distal end of the flexible distal catheter tube such that the proximal end is contained in the tube and the rotating tip protrudes therefrom. The rotating tip is preferably built in a triangular shape, with three longitudinal teeth separated by curved fluted side surfaces to allow for greater maneuverability by enabling the catheter tip to roll over the endocardial surface. The teeth provide better frictional traction and electrical contact with the endocardial surfaces. In one embodiment, the distal 10 mm consists of three such teeth symmetrically placed (120° apart). The teeth are curved to further improve traction during rotation of the tip.

The proximal portion of the rotating tip electrode inside the flexible tubing has a micro bearing system of two safety rings that anchor the rotating tip to the bearing, as well as a fixation and seal between the rotating tip and the catheter. The portion of the rotating tip inside the flexible tubing has two (~1 mm wide) rings that provide the fixation and seal between the rotating tip and the catheter. The proximal portion of the tip has a shaft with a disc that is incorporated into the bearing system. The bearing fits over the shaft of the tip and contains the two rings which serve as an anchor for the catheter tip mechanism. In addition to the bearing system, anchor rings, and the rotation wire, two safety wires are preferably attached to the bearing system and are connected to T-shaped pins that are imbedded 10 mm proximal to the tip and serve as additional safety to prevent the tip from dislodging from the catheter shaft.

The rotational torque for the tip is transmitted via a high-stainless steel wire, typically 0.358 mm, which is fixed to the tip. The wire is contained in a tubular sheath of a reduced friction material such as polytetrafluoroethylene (PTFE) that allows it to rotate with minimal or reduced friction.

The rotational torque transmitting wire and the low friction tubing are threaded through the central shaft of the flexible and rigid portions of the catheter and extends out of the catheter tubing through a radial opening at a point spaced distally from the handle and is connected to a hand-operated rotatable lateral adjustment control knob mounted from the catheter handle at a fixed distance therefrom. Rotation of the knob left or right transmits and applies rotational torque to rotate the catheter tip. The rotational knob is designed to rotate freely when it is pushed down and lock in position when released.

The high-torque wire may be used for rotational control, delivery of the radio frequency electrical current to the rotating tip for ablation, and as the distal recording pole for receiving myocardial tissue electrical activity for recording and mapping. Electrical conduction to the high-torque rotation wire is accomplished via a brush-like pick off mechanism located in the rotation control knob.

Additional electrodes, preferably 2 or 3 ring electrodes, may be serially spaced proximally from the tip electrode, typically starting 2 mm behind the tip electrode and spaced about 2 mm apart. All of the electrodes are connected to an input/output device, typically an electrical phono jack type connector, by thin low resistance wire conductors. The phono jack or other input/output connector is attached to the handle. The electrodes can be connected to a recording system which measures and displays cardiac depolarization potentials sensed within the involved cardiac chamber. This system can be used to map the earliest activation time indicating the most desirable location for tissue ablation. The tip electrode is used for both electrical mapping when connected to the recording equipment and to deliver the ablation energy when it is connected to an energy source.

The system also includes a vertical deflection control wire. The vertical deflection wire controls the deflection of the tip in a plane parallel to the main catheter tube (vertical deflection). It includes a wire, preferably of stainless steel, inserted into the deflectable portion of the catheter in an off-center position and anchored to the catheter side wall as by a T-shape stainless steel pin just below the tip electrode system.

The vertical deflection control wire is threaded through the catheter to the handle and anchored to a longitudinal (slidably) movable portion of the handle. Sliding the handle member on the shaft portion results in vertical deflection changes of the flexible catheter tip. Tension in the vertical deflection wire inherently causes the tip to deflect since the insertion position of this wire is off center and in the side of the flexible portion of the catheter.

Rotation of the catheter tip is achieved using highly torqueable wire which is flexible only at the end and which is inserted into the flexible deflectable distal portion of the catheter. The proximal portion of this wire is significantly more rigid.

BRIEF DESCRIPTION OF THE DRAWINGS

In the drawings, wherein 11 like parts are numbered the same throughout.

DETAILED DESCRIPTION

Figure 1:
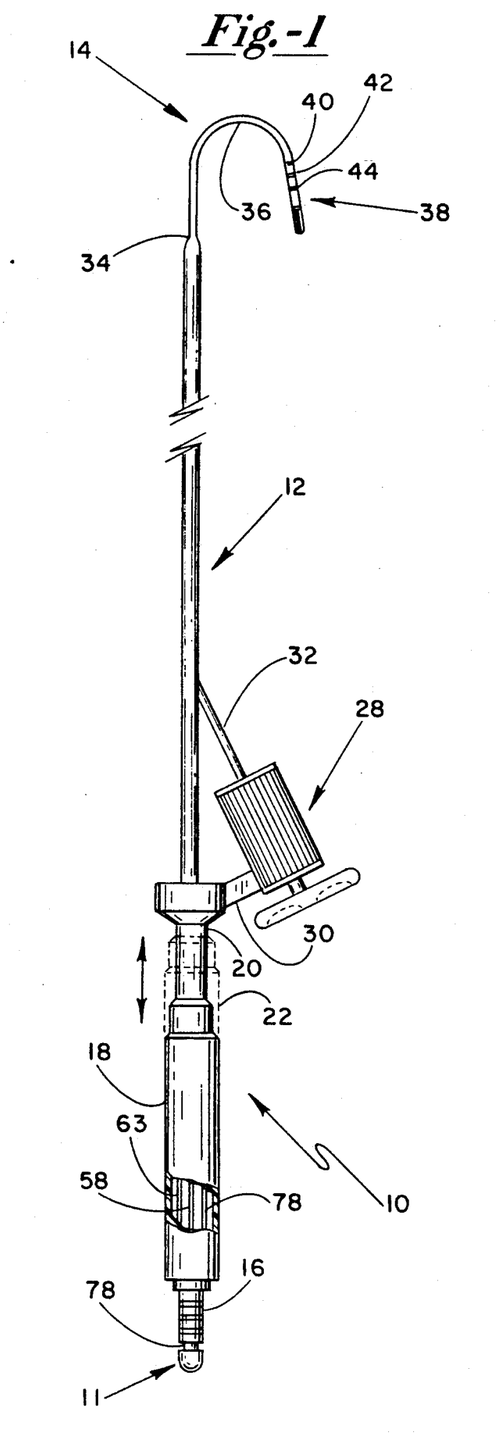
FIG. 1 is a side view of the catheter system, partially fragmented with parts in section.

The rotating tip tissue ablation catheter system is shown in FIG. 1 and includes a handle portion shown generally at 10, a central, relatively rigid tubular section 12, and a flexible distal maneuverable distal catheter section 14. The central section 12 is shown broken as it depicts the long main body of the catheter.

The handle portion further includes an electrical jack-type plug-in device 16 having multiple input/output pick off points associated with conductors discussed below. An outer hand grip section 18 in the handle portion is made freely adjustable for a distance along the longitudinal axis of the handle relative to the inner tubular handle section 20. The distance of adjustment is further illustrated in phantom at 22. The handle includes a hand-operated rotatable lateral tip deflection control knob shown generally at 28, is fixed in position spaced from the handle by a mounting member 30 and connected with the central tubular section by a tubular member 32. The knob itself is longitudinally and rotationally adjustable and will be more fully described below. The main catheter tube 12, in turn, is connected with the flexible, maneuverable distal tip section 14, which may be the same or of a slightly smaller diameter, by a transition 34. The flexible tip section further includes a proximal segment of flexible reinforced polymer catheter tubing 36 which connects the distal end of the main catheter tube 12 and the catheter tip system 38 containing the electrode and the rotating tip system. The tubing segment 36 may be of any convenient length, typically about 4 to 8 centimeters, depending on the desired use. The tubing segment may be of any biologically compatible, relatively inert polymeric material having the requisite strength and flexibility together with the ability to be incorporated with other catheter materials may be reinforced with materials to achieve needed characteristics and generally has an ID of about 3 mm or less.

Figure 2A:
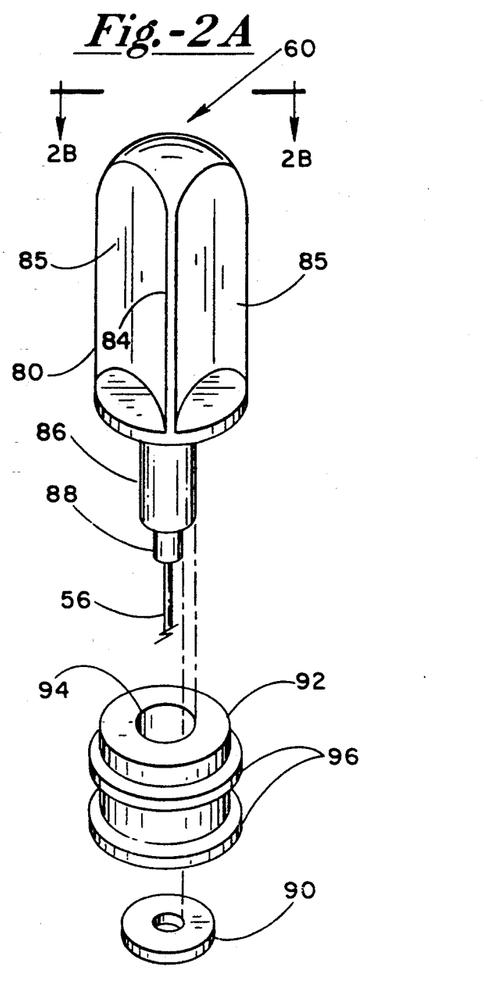
FIG. 2A is an enlarged exploded view of the rotating tip portion of the catheter of FIG. 1.
Figure 2B:
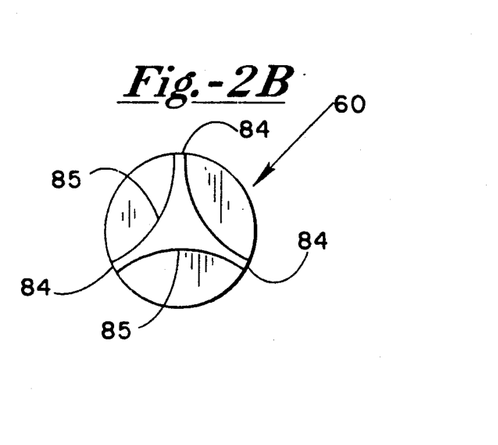
FIG. 2B is an end view of the rotating tip of FIG. 2A.
Figure 3:
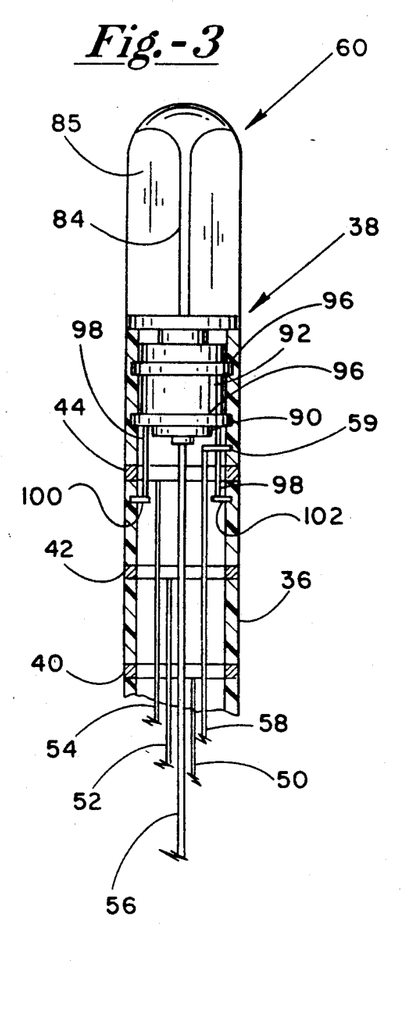
FIG. 3 is a greatly enlarged side view of the tip system rotor of FIG. 1.

As shown, enlarged for greater clarity in FIGS. 2A, 2B and 3, the catheter tip system includes a plurality of electrode bands 40, 42 and 44 which are in electrical communication with the external environment of the tip and with respective insulated electrical conductors 50, 52 and 54. The conductors are threaded through the catheter tubes 36 and 12 and the handle to separate pick-offs on the jack 16.

Rotating tip 60 of the ablation electrode system 38 may be adapted to be an input to a recording system in a mapping mode or an output from a source of high frequency electrical power via conductor or conductors 56, when operated in an ablating mode, as desired. As will be described in greater detail below, rotation of the tip member 60 is achieved by high torque wire 56 which is connected to the tip electrode at the distal end and threaded through the central core of the catheter tubing and proximally through the tubing 32 to the lateral control knob 28.

A vertical tip deflection control wire 58 is inserted into the deflectable portion of the catheter in an off-center position and has a distal extremity anchored to the side wall of the catheter by a T-shaped stainless steel pin 59 (FIG. 3) just below the tip electrode system 38. The vertical deflection control wire 58 is threaded through the central lumen of the catheter to the handle 10 and the proximal end anchored to the movable portion of the handle 18. Sliding the handle member 18 on the shaft portion thereby results in vertical deflection changes of the flexible catheter tip.

Figure 4:
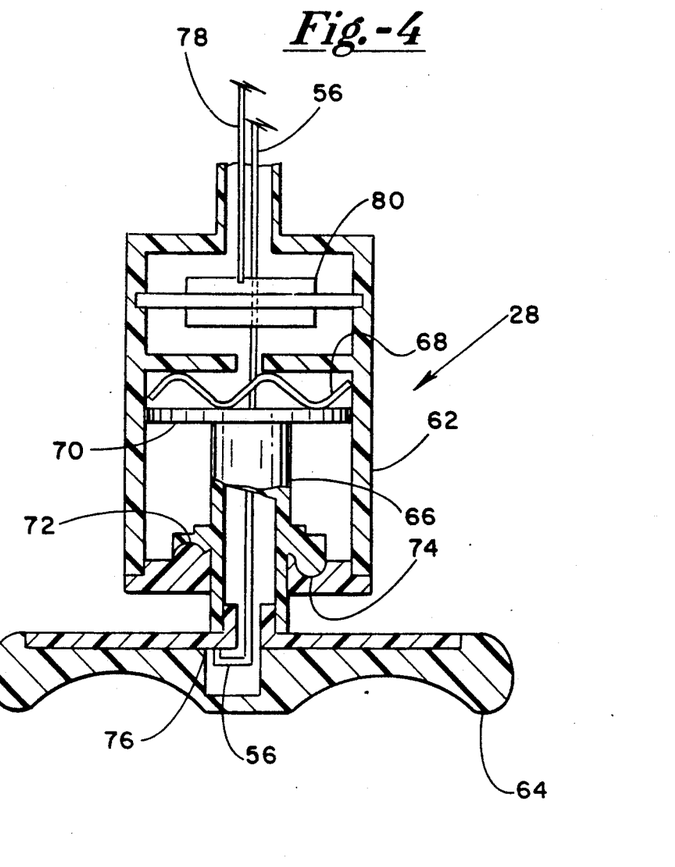
FIG. 4 is an enlarged view, partially in section, of the control knob of FIG. 1.

The hand-operated rotatable lateral tip rotation control knob system shown in detail in FIG. 4 is also shown in FIG. 1. The hand-operated knob system 28 includes an outer cylindrical member 62, a finger-operated bidirectional adjustable knob member 64, connected to an internal cylinder 66. A spring 68 pushes against a stop member 70 which, in turn, acts on cylinder 66 to urge the knob member upward with respect to the handle 62 engaging the locking ball and socket type splines 72 and 74. The control wire 56 traverses the knob system and is anchored on the knob at 76 so that the rotational torque applied to the control wire 56 is directly controlled by the rotation of the knob 64. A power take-off system is provided to supply electric power from a contact on the phono jack 16 through connecting conductor 78 to the control wire 56 utilizing a transfer conductor 80 through which the wire 56 is threaded so that constant contact is maintained in the manner of motor brushes or the like.

The rotating tip system is particularly depicted in the exploded view and end view including FIGS. 2A and 2B and in FIG. 3. As shown in FIG. 3, the tip system 38 includes the rotating tip member 60 which protrudes from the distal end of the flexible distal catheter tube 36, the remainder or proximal portion of the rotating tip system being imbedded within the flexible deflectable catheter tube 36. As seen better in the exploded view of FIGS. 2A and 2B, the exposed portion includes the rotating tip head which contains three tooth members as at 84 based symmetrically about the center axis, approximately 120° apart. The area between the teeth, as at 85, is fluted or contoured to further accentuate the ability of the teeth to provide traction for the tip. The rotating head is attached to an integral shaft 86 which may be on the order of 5 mm in length and a further, smaller diameter (approximately 1 mm) shaft 88 which carries a ring member 90 that is directly connected to the high-torque rotational wire 56. The ring is fixed to the shaft as with silver soldering, preventing the tip from disengaging from the bearing system 92.

The shaft 86 is designed to be journaled within a bearing system 92 (FIG. 2A) which contains a permanently lubricated cylindrical central opening 94 and a pair of rings 96 which are adapted to hold the bearing assembly 92 stationary with respect to the tube 36 as the ends imbed in the sides of the tubing when the proximal end of the system is inserted into the flexible catheter tube. The shaft 86 and matching internal surface of the cylindrical opening 94 are preferably made of self-lubricating material such as PTFE, or the like.

The rotating tip and bearing system are inserted into the flexible distal tubular catheter system 36 and held in place by the bearing rings 96. As shown in FIG. 3, additional wires 98 may be attached to the bearing unit 92 and further anchored in the side wall of the catheter tube 36, as at 100 and 102, to act as safety anchors and further prevent dislodgment of the bearing unit from the distal end of the catheter tube during use.

While it will be appreciated that any mechanical equivalent set-up can be used which accomplishes the aims of the hand-operated rotatable knob control system 28, the one pictured in FIG. 4 operates basically in the following manner. The knob 64, together with the attached internal cylinder 66, is reciprocally adjustable in the longitudinal direction against the return spring 68 such that when the handle 64 is pushed in, the plurality of rounds and sockets as at 72 and 74 disengage, allowing cylinder 66 to be rotated with respect to the housing member 62. The end of the wire 56 is fixed in position in the member 64 at 76 such that rotation of the knob 64 applies a rotational torque in the desired direction to the control wire 56, which is, in turn, transmitted to rotate the tip 60 as desired. The spring 68 normally maintains the rounds and sockets in an enmeshed position such that relative rotation is otherwise precluded thereby maintaining the rotational position of the tip 60 constant.

In operation, the catheter system is introduced by an incision into the femoral artery and routed through the vascular system into the desired chamber of the patient's heart. Once the proper chamber is reached, reciprocal movement of the handle 18, together with depression and rotation of the knob 64, produces precise control of intricate vertical and lateral movement of the tip member 60 such that any point on the wall of the chamber is readily accessible to the electrodes. The electrode members 40, 42, 44, and 60 can be utilized to map the cardiac depolarization potentials throughout the chamber, thereby locating and mapping the early activation site. The tip electrode 60 is used to transfer the energy for tissue ablation, and may, in some cases, also be used in a mapping mode.

Great precision in the lateral movement of the rotating catheter tip 60 against chamber walls is possible with the catheter system of the invention, especially in the ventricle chambers where the fluted teeth 84 of the rotating tip 60 facilitate placement and movement along the walls. This makes catheter-initiated ablation of tissue with respect to curing heart arrhythmias much easier and more precise. The procedure is much more practical than previous systems.

This invention has been described herein in considerable detail in order to comply with the Patent Statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

I claim:

1. A cardiac arrhythmia mapping and ablation catheter comprising;
    a relatively short, flexible distal catheter section for entering and selectively negotiating inner surfaces of any cardiac chamber, having a distal end and describing a lumen through a length thereof;
    deflection element means for controlling deflection of the distal catheter section;
    deflection element control means for controlling the deflection element means;
    a rotatable conducive tip electrode member carried by and journaled in the distal end of the distal catheter section and adapted to rotate independently of and relative to the distal catheter section to further engage and roll over an internal surface of a heart chamber of interest thereby guiding the distal catheter section; and
    rotation control means for producing and controlling independent rotation of the rotatable tip electrode member.

2. A cardiac arrhythmia mapping and ablation catheter comprising:
    an elongated main catheter body member having a proximal and a distal end and describing a continuous internal lumen extending therebetween and having an outside diameter small enough to pass through a vascular system from an introducer site to a cardiac chamber of interest, said main catheter body member having a control handle affixed to said proximal end thereof;
    a relatively short, flexible distal catheter section extending from the distal end f the main catheter member for entering and selectively negotiating an inner surface of any cardiac chamber, having a distal end and describing a lumen through a length thereof;
    deflection element means for controlling deflection of the distal catheter section;
    deflection element control means for controlling the deflection element means;
    a rotatable conductive tip electrode member having a peripheral and distal end carried by and journaled in the distal end of the distal catheter section and adapted to rotate independently of and relative to the distal catheter section to further engage and roll over an internal surface of a heart chamber of interest thereby guiding the distal catheter section;
    rotation control means for producing and controlling independent rotation of the rotatable tip electrode member; and
    electrical conductor means forming a conductive path connecting the rotatable tip electrode member to a proximal external connection or alternately receiving electrical signals from the rotatable tip electrode member and delivering electrical Ablation impulses to the rotating tip electrode member from a remote input/output device.

3. The cardiac arrhythmia mapping and ablation catheter of claim 2 further comprising:
   a plurality of spaced, external conductive ring electrodes carried in the distal portion of the distal catheter section proximally spaced form the rotatable tip electrode member; and
   conductor means connected to each conductive ring electrode for receiving electrical impulses from the conductive ring electrodes and delivering electrical ablation impulses to the ring electrodes 4. The cardiac arrhythmia mapping and ablation catheter of claim 2 wherein the rotation control means for producing and controlling the rotation of the rotatable tip electrode member further comprises:
   a torqueable rotation control wire having a proximal and a distal end headed within the distal catheter section lumen, the distal end of the rotation control wire being fixed in relation of the rotatable tip electrode member such that an application of rotational torque of the control wire produces a corresponding rotation of the rotatable tip electrode member relative to the distal catheter section;
   means for applying rotational torque to the rotation control wire thereby rotating only the rotatable tip electrode member.

5. The cardiac arrhythmia mapping and ablation catheter of claim 4 further comprising:
   bearing means for receiving a rotatable shaft journaled therein fixed in the distal end of the flexible tubular distal catheter section;
   shaft means for carrying the rotatable tip electrode member attached to the proximal end of the rotating tip electrode member and journaled for rotation in bearing means;
   retention means for retaining the shaft means journaled in the bearing means; and
   wherein the rotation control wire is fixed to the shaft means.

6. The cardiac arrhythmia mapping and ablation catheter of claim 5 wherein the rotated tip electrode member further comprises a plurality of radially spaced longitudinally oriented traction teeth adapted to engage an internal surface of a heart chamber 7. The cardiac arrhythmia mapping and ablation catheter of claim 6 wherein the plurality of teeth comprises three symmetrically spaced teeth with fluted indentations therebetween.

8. The cardiac arrhythmia mapping and ablation catheter of claim 5 wherein the means for applying rotational torque of the rotation control wire is a self-locking, hand releasable nd hand rotatable knob system connected to the proximal end of the rotation control wire.

9. The apparatus of claim 8 wherein the self-locking, hand-rotatable knob system further comprises a self-locking, hand-rotatable control knob spaced form h control handle and attached to the rotation control wire in a manner such that rotation of the knob left or right applies a corresponding rotational torque to the lateral deflection control wire which is transmitted to the rotatable tip electrode member and producing rotation bin the corresponding direction.

10. The apparatus of claim 9 wherein the electrical conductor means for receiving electrical signal form the rotatable tip electrode member and delivering electrical signals to the rotating tip electrode member is the rotation control wire.

11. The apparatus of claim 5 wherein the electrical conductor means for receiving electrical signals form the rotatable tip electrode member and delivering electrical signals to the rotating tip electrode member is the rotation control wire.

12. The apparatus of claim 11 wherein the rotation control means further comprises voltage pick off means for transmitting voltage to and from the rotational control wire.

13. The cardiac arrhythmia ablation catheter of claim 19 wherein the teeth comprise three gently fluted teeth spaced about 120° apart.

14. The cardiac arrhythmia ablation catheter of claim 5 wherein the bearing means is connected to a safety anchor in the crystal catheter section.

15. The cardiac arrhythmia mapping and ablation catheter of claim 4 wherein the rotatable tip electrode member further comprises a plurality of radially spaced longitudinally oriented traction teeth adapted to engage an internal surface of a heart chamber.

16. The apparatus of claim 4 wherein the electrical conductor means or receiving electrical signals from the rotatable tip electrode member and delivering electrical signals to the rotating tip electrode member is the rotation control wire.

17. The apparatus of claim 16 wherein the rotation control means further comprises voltage pick off means or transmitting voltage to and from the rotational control wire.

18. The cardiac arrhythmia ablation catheter of claim 17 wherein the rotatable tip electrode member further comprises a plurality of radially spaced longitudinally oriented traction teeth adapted to engage an internal surface of a heart chamber.

19. The cardiac arrhythmia ablation of claim 2 wherein the rotatable tip electrode member further comprises a plurality for axially spaced longitudinally oriented traction teeth adapted to engage an internal surface of a heart chamber.

20. A catheter system for use in mapping and performing arrhythmogentic tissue ablation comprising:
   a central catheter including an elongated, flexible tube having a proximal end and a distal end, having an outside diameter small enough to pass through an arterial vascular system form an introducer site to a coronary chamber of interest, and further describing an internal lumen of a relatively large size extending form the proximal nd to the distal end and having a tube wall sufficient to provide torque transmission required to enable routing of the catheter through a vascular system;
   a relatively short distal catheter section including an electrode distal tip section connected tot h distal end of the central catheter comprising a flexible plastic tube connected to the distal end of the central catheter having an outside diameter smaller than that of the central catheter and able to pass into any chamber having a proximal; and a distal end and further describing an internal lumen extending from the proximal end to the distal end;
   a deflection control system including deflection control wire means for deflection of the distal catheter section in a controlled manner;
   a rotatable electrical conductive distal tip electrode member carried by and journaled in the distal end of the lumen of the distal catheter section and adapted to rotate independently of the distal catheter section and to engage and roll over an internal surface of a heart chamber of interest;

a plurality of spaced, external conductive ring electrodes carried in the distal tip section of the distal catheter section proximally spaced form the rotatable distal tip electrode;

conductor means connected to each conductive ring electrode for receiving electrical impulses for the conductive ring electrodes and delivering electrical ablation impulses to the ring electrodes;

a rotation control means including a torqueable rotation control wire threaded within the digital catheter section lumen and having a distal end fixed in relation to the rotatable tip electrode member such that an application of rotational torque to the control wire produces a corresponding free rotation of the rotatable tip electrode member;

shaft means for carrying the rotatable tip electrode member connected to the proximal end of the rotatable distal tip electrode member;

bearing means for reducing friction in which the shaft means connected to the rotatable tip member is journaled for rotation disposed in the distal catheter section;

wherein the rotation control wire further provides an electrical conductor means for receiving electrical impulses from the rotatable tip electrode member and delivering electrical ablation impulses to the rotating tip electrode member form outside of the catheter.

21. A method of electrically mapping and ablating cardiac tissue with a catheter, the method comprising the steps of:

providing an electrically mapping and ablating cardiac catheter comprising:

a relatively short, flexible tubular distal catheter section for entering and navigating inner surfaces of a cardiac chamber of interest describing a lumen through a length thereof and carrying a distal tip electrode system including a deflection wire and hand operated deflection wire control means for enabling and controlling deflection of the distal tip electrode system;

a freely, independently rotatable tip electrode member and hand operated tip electrode rotation control system, the tip electrode being mounted at and journaled in the distal end of the distal catheter section lumen and adapted to engage and roll over an internal surface of a part chamber of interest;

electrical conductor means for receiving electrical mapping impulses form and delivering electrical ablation impulses to the rotatable tip electrode member form outside of the catheter;

introducing the catheter system into a vascular system of a patient at an introducer site and routing it through the vascular system into a desired chamber of a patient's heart;

using the deflection wire control mans and rotation control system in conjunction with the rotatable tip electrode member to explore a wall of a chamber of interest with vertical and lateral movement of the rotatable tip electrode member such that electrical activity of the internal wall of a chamber can be mapped;

applying radio frequency ablative electric current to the tip electrode member to abate tissue at early activity where indicated.

* * * * *

UNITED STATES PATENT AND TRADEMARK OFFICE
CERTIFICATE OF CORRECTION

PATENT NO.  : 5,242,441          Page 1 of 2
DATED       : September 7, 1993
INVENTOR(S) : Boaz Avitall It is certified that error appears in the above-indentified patent and that said Letters Patent is hereby corrected as shown below:

In column 8, line 21, delete "conducive" and insert -- conductive -- ; line 42, delete "f" and insert -- of -- ; line 52, delete "peripheral" and insert -- proximal; line 63, delete "or" and insert -- for -- ; line 65, delete "Ablation" and insert -- ablation -- .

In column 9, line 5, delete "form" and insert -- from -- ; line 16, delete "headed" and insert -- threaded -- ; line 18, delete "of" and insert -- to -- ; line 20, delete "of" and insert -- to -- ; line 30, delete "tubular"; lines 32 and 33, delete "rotating" and insert -- rotatable; line 34, after "in", insert --- said -- ; line 50, delete "of" and insert -- to -- ; line 51, delete "nd" and insert -- and -- ;

; line 61, delete "bin" and insert -- in -- ; line 64, delete "signal form" and insert -- signals from -- .

In column 10, line 2, delete "form" and insert -- from -- ; line 15, delete "crystal" and insert -- distal -- ; line 28, delete "or" and insert -- for -- ; line 37, delete "for axially" and insert -- of radially spaced -- ; line 45, delete "form" and insert -- from -- ; line 48, delete "form" and insert -- from -- ; line 48, delete "nd" and insert -- end -- ; line 53, delete "electrode" and insert -- electroded -- ; line 53, delete "tot h" and insert -- to the -- ; line 58, delete "proximal;" and insert -- proximal -- .

UNITED STATES PATENT AND TRADEMARK OFFICE
CERTIFICATE OF CORRECTION

PATENT NO. : 5,242,441
DATED : September 7, 1993
INVENTOR(S) : Boaz Avitall

It is certified that error appears in the above-indentified patent and that said Letters Patent is hereby corrected as shown below:

In column 11, line 5, delete "form" and insert -- from -- ; line 6, after "electrode", insert -- member -- ; lne 8, delete "for" (second occurrence), and insert -- from -- ; line 12, delete "digital" and insert -- distal -- ; line 29, delete "form" and insert -- from -- .

In column 12, line 16, delete "part" and insert -- heart -- ; line 19, delete "form" and insert -- from -- ; line 21, delete "form" and insert -- from -- ; line 22, delete "system"; line 26, delete "mans" and insert -- means -- .

Signed and Sealed this

Thirty-first Day of May, 1994

Attest:

BRUCE LEHMAN

Attesting Officer          Commissioner of Patents and Trademarks

UNITED STATES PATENT AND TRADEMARK OFFICE
CERTIFICATE OF CORRECTION

PATENT NO. : 5,242,441
DATED : September 7, 1993
INVENTOR(S) : Boaz Avitall

It is certified that error appears in the above-indentified patent and that said Letters Patent is hereby corrected as shown below:

Column 9, line 56, delete "from said" and insert --from the--.
Column 9, line 59, delete "lateral" and insert --rotation--.

Signed and Sealed this

Twenty-third Day of August, 1994

Attest:

BRUCE LEHMAN

Attesting Officer     Commissioner of Patents and Trademarks